United States Patent [19]

Weisenthal

[11] Patent Number: 5,149,527
[45] Date of Patent: Sep. 22, 1992

[54] IMMUNOPOTENTIATING PROTOCOL FOR CHEMOTHERAPY-RESPONSIVE TUMORS

[75] Inventor: Larry M. Weisenthal, Huntington Beach, Calif.

[73] Assignee: Oncotech, Inc., Irvine, Calif.

[21] Appl. No.: 584,272

[22] Filed: Sep. 18, 1990

[51] Int. Cl.$^5$ ............................................. A61K 37/02
[52] U.S. Cl. ..................................... 424/85.2; 514/2
[58] Field of Search .......................... 424/85.2; 514/2

[56] References Cited

FOREIGN PATENT DOCUMENTS 8701397 12/1987 PCT Int'l Appl. .

OTHER PUBLICATIONS

Fizames et al., *J. Biol. Resp. Mod.* Aug. 1989, 8(4) pp. 397–408 (Abstract).
Tokunaga, *Ganto Kagaku Ryoho*, May 1987 14 (5 pt 2) pp. 1358–1366 (Abstract).
Adler et al, *J. Natl Cancer Inst.* Feb. 1985, 74(2) pp. 429–436 (Abstract).
Immunological Mechanisms in Cancer Treatment Klippel et al (Abstract)–monograph pp. 79–158.
Coley, *Am. J. Med. Sci.* (1893) 103:487–511.
Coley, *Trans. Am. Surg. Assoc.* (1894) 12:183–212.
Oettgen et al., "Important Advances in Oncology" B. T. DeVita, Jr., et al., eds., J. B. Lippincott Company, Philadelphia, Pa. pp. 105–132.
Hersh, "Immunity to Cancer" A. E. Reif et al., Academic Press, Orlando, Fla. (1985) pp. 443–452.
Yamamoto et al., *Cancer Res.* (1987) 47:2008–2013.
Yamamoto et al., *Cancer Res.* (1988) 48:6044–6049.
Ruszala-Mallon et al., *Int. J. Immunopharmacol.* (1988) 10(5):497–510.
Cockett et al., *Proc. Clin. Biol. Res.* (1989) 303:455–462.
Mayer, *New Eng. J. Med.* (1990) 322(6):399–401.

*Primary Examiner*—Merrell C. Cashion, Jr.
*Assistant Examiner*—Choon Koh
*Attorney, Agent, or Firm*—Morrison & Foerster

[57] ABSTRACT

Immunopotentiating compositions which are useful in causing tumor necrosis and/or regression in subjects who have previously received successful therapy which destroys tumors and stimulates cytotoxic macrophages are described. The immunopotentiators are administered at a time when formation of macrophages specifically cytotoxic for the tumor have been generated by previous therapy.

9 Claims, 16 Drawing Sheets

Exhibit - Agents for which Oncotech may be able to define a Medical Use, based upon its laboratory studies.

ImuVert (Cell Technology Biologic Response Modifier)
gamma interferon
tumor necrosis factor alpha
levamisole
Swainsonine
CL 246,738 (American Cyanamid-Lederle Laboratories)
CL 259,763 ("              ")
ADA-202-718 (2,2'-[1,2-ethanediylbis(dithio)bisethanol
azimexone
(1-[1-(2-cyano-1-azirdinyl)-1-methyl)-2-aziridinecarboxamide
Imuthiol (diethyl carbamodithioic acid sodium salt)
Isoprinosine (Newport Pharmaceuticals)
NPT 15392
hydroerthranol (NPT-15392)
Pimelautide
ABPP
Therafectin
BCG (Bacillus Calmette-Guerin)
BCG-MER (methanol extractable BCG)
C.Parvum (Cornyebacterium parvum)
Bru-Pel (Brucella abortus extract)
Pseudogen (Pseudomonas aeruginosa)
Nocardia rubra (cell wall extract N-CWS)
Picibanil (OK-432, Streptococcus pyuogenes) (Chugai pharmaceuticals)
Biostim (Roussel-Ucalf)
Peptidoglycan (")
WSA(")
LPS(")
Monophosphoryl lipid A (detoxified LPS)(")
Krestin (PSK) (Kureha/Sankyo pharmaceuticals)
Glucanl
Lentinan (Ajinomoto/Morhita/Yamanouchi)
Pustuoln
Levan
Mannozym
Bestatin (Nippon Kayaku)
Tuftsin (Abic)
Muramyldipeptide (Immunotherapeutics, Syntex)
FK-565 (Fujisawa)
HP-5
Therafectin (Greenwich)
Cimetidine (SKF)
Pyrimidinols (ABPP) (Upjohn)
Anthraquinones (Tilorone-Merrel Dow)
Forphenicinol
LS-216 Pharmacia
Azimexone BM 12.531

FIG. I-I

```
Cimexone
BAYi 7433 (Bayer)
Nafazatrom (BAY g-6575) (Bayer)
NED 137 (Monsanto)
Alkyl-lysylphospholipids
    lysophosphatidic acid, oleoyl
    lysophophatidylcholine (lysolecithin)
    lysophosphatidylcholine,decanoyl
        "                ,heptadecanoyl
        "                ,gamma-o-hexadecyl
        "                ,oleoyl
        "                ,stearoyl
    lysophosphatidyl-ethanolamine
    lysophosphatidyl-glycerol
    lysophosphatidyl-inositol
    lysophosphatidyl-serine
    phosphatidylcholine,acetyl-gamma-o-hexadecyl
    phosphatidylcholine,beta-acetyl-gamma-o-(octadec-9-cis-enyl)
    phosphatidylcholine,beta-acetyl-gamma-oleoyl
    phosphatidylcholine,diheptanoyl
    phosphatidylcholine,di-o-hexadecyl
    phosphatidylcholine,beta-o-methyl-gamma-o-hexadecyl
    phosphatidylcholine,beta-o-methyl-gamma-o-octadecyl
    phosphatidylethanolamine
    phosphatidyl-glycerol
    phosphatidyl-inositol
MVE-2
sodium diethylthiocarbamate
Thiabendazole
Methylfurylbutyrolactones (Nafocare B) (American Biotech)
Poly IC
Poly ICLC
Poly AU
Ampligen
```

FIG. I-2

IMMUNOPOTENTIATING PROTOCOL FOR CHEMOTHERAPY-RESPONSIVE TUMORS

TECHNICAL FIELD

The invention relates to treatment of tumors in animal subjects, including humans. The efficacy of the immunopotentiating therapy of the invention depends on the formation of macrophages specifically cytotoxic for tumor cells by virtue of previous destruction of some of the tumor cells in a therapeutic regime.

BACKGROUND ART

There have been numerous previous attempts to explore the effects of immunopotentiation in general on the growth of tumor cells in humans. Observations were made as early as the 1890s that in some instances, although a rather small percentage, administration of immunopotentiating agents to patients resulted in remission of their tumors (Coley, W. B., *Am J Med Sci* (1893) 105:487; *Trans Am Surg Assoc* (1894) 12:183; *Proc R Soc Med (Surg Sect)* (1909) 3:1; for reviews, see Oettgen, H. F., et al., in "Important Advances in Oncology," DeVita B. T., Jr., et al., eds., J. B. Lippincott Company, Philadelphia, Pa. (1987) pp. 105–132; Hersh, E. M., in "Immunity to Cancer," Reif, A. E., et al., eds., Academic Press, Orlando, Fla. (1985) pp. 443–452.

In addition, it has been observed that inflammation of cancer cells, but not of normal cells in a subject by administration of bacterial cells or their constituents can result in tumor regression. This has been assumed due to the differing nature of the components released from cancer cells during inflammation as compared to normal cells (Yamamoto, N., et al., *Cancer Res* (1987) 47:2008–2013; Yamamoto, N., et al., *Cancer Res* (1988) 48:6044–6049). In addition, a number of immunopotentiators have been considered as potential therapeutic agents for not only infectious diseases, but also in the treatment of neoplasms (Ruszala-Mallon, V., et al., *Int J Immuno Pharmac* (1988) 10:497–510).

Despite this modest early success at the turn of the century, the use of immunopotentiators for treatment of tumors has not been actively pursued in view of the putatively more effective methods of radiotherapy, chemotherapy, and surgery. Nevertheless, some attention has been paid sporadically to this approach, and the results of studies heretofore have been inconclusive as to describing ways to predict success or failure using such treatments and therefore to devise protocols which will assure success. Local treatment of noninvasive bladder cancer with the putative immunostimulator BCG has, however, been reported (Cockett, A. T., et al., *Proc Clin Biol Res* (1989) 303:455). There is also recent evidence that the concomitant administration of 5-fluorouracil and levamisole (an immunopotentiator) may be effective in the treatment of Duke's C colon cancer (Moertel, C. G., et al., *New Engl J Med* (1990) 322:399–401). Although levamisole is known to have immunopotentiating properties, it is not clear whether the effectiveness of this combination is due to immunopotentiation or to some other form of synergy (ibid).

One of the nonspecific immunopotentiators which has been used recently is a preparation from the bacterium *Serratia marcescens* which contains small ribosome particles and membrane vesicles in a suspending buffer. This preparation is in clinical trials and utilizes the trademark "ImuVert," is described in PCT/US87/01397, and is marketed by Cell Technologies of Boulder, Colo. Although this preparation was used in a number of studies in support of the invention described and claimed herein, it is merely representative of a large class of immunopotentiators which are effective with respect to macrophages.

It is also known that tumor cell preparations may contain effector cells derived from the immune system. Generally, these may be classified as lymphocytes and macrophages. The presence of macrophage effector cells at the site of the tumor is essential for the success of the method of the invention as will be described further below.

It has now been found that immunopotentiators which are directed to macrophage populations are effective in causing tumor necrosis if the tumor is of a type that can be successfully treated using chemotherapy or other treatment methods which result in tumor cell destruction and provided that the tumor has actually been treated with chemotherapy or said alternative protocols prior to the administration of the immunopotentiator.

DISCLOSURE OF THE INVENTION

The invention is directed to protocols for effecting tumor regression and/or necrosis in animal subjects. In particular, it involves pretreatment of the tumor with a tumor destroying protocol, such as a chemotherapeutic agent, radiation, or hyperthermia, for a time and in a manner effective to cause the formation of tumor-specific cytotoxic macrophages and other tumor infiltrating effector cells and then to administer a quantity of immunopotentiator specific for these macrophages which effectively results in lysis of the tumor. Essentially, the tumor-destructive protocol that precedes treatment with immunopotentiator is used to provide "vaccination in situ."

BRIEF DESCRIPTION OF THE DRAWINGS

FIG. 2 shows a summary of results of immunopotentiator activity on various types of tumor substrates in treated and untreated patients.

MODES OF CARRYING OUT THE INVENTION

Figure 2:
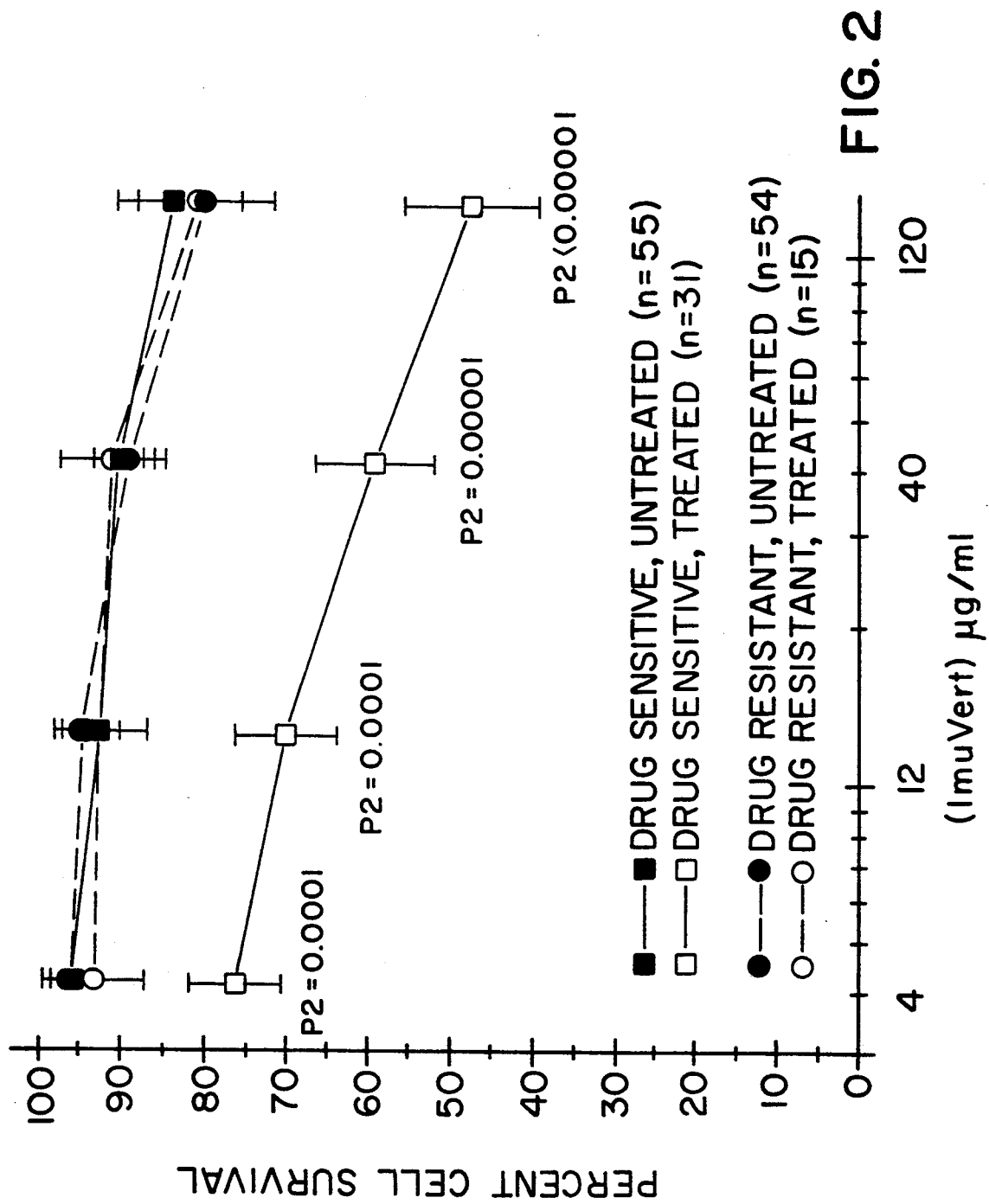
FIG. 1-1, 1-2 contains a partial listing of immunopotentiating agents which affect macrophages and which are suitable for the practice of the invention.

The invention provides a predictable protocol for the treatment of animal subjects to effect necrosis and/or regression of malignant tumors. As used herein, "animal" generally refers to mammals and birds, especially domesticated mammals and birds, and to humans. Thus, the method is applicable to household pets, agricultural mammals and poultry and, most preferably, to human beings.

The method of the invention is directed to a subset of malignant tumors which is responsive to tumor destructive protocols, such as chemotherapy or radiation therapy. Specifically with respect to *presently* available chemotherapeutic methods, tumors which are responsive to chemotherapeutic treatment generally include hematologic neoplasms, pediatric neoplasms, and certain adenocarcinomas, such as those from breast and ovary. Adenocarcinomas which are refractory to chemotherapy include those of colon, lung and kidney. Tumor sensitivity to radiation and/or hyperthermia varies according to mode of administration. Systemic treatment (i.e., whole body or hemibody administration) has unpredictable, but usually low, efficacy. Local therapy directed at discrete tumor lesions is usually effective to produce at least partial destruction of the neoplasm. In individual cases, successes can be empirically determined.

While not wishing to be bound by any theory, it is believed that the requirement for susceptibility to and treatment by chemotherapy or other destructive protocol is a result of the necessity for the formation of tumor-specific cytotoxic effector cells, especially macrophages, in connection with the tumors. This process presumably occurs when sufficient tumor necrosis has been effected by appropriate protocols to provide a multiplicity of tumor-specific antigens for stimulation of the immune system. Whatever the mechanism, however, the method of the invention requires, prior to the administration of the immunopotentiator, significant destruction of the tumor cell population using a successful therapeutic protocol.

Provision of a suitable patient population, therefore, for the method of the invention by treatment of individuals with tumor-destructive therapy where the therapy will be at least moderately successful is an essential feature of the invention. Although it is possible simply to administer such therapeutic protocols to subjects presumed to be receptive to these treatments, and then to administer the immunopotentiator only to the successes, it is possible, and more rational, to design therapeutic treatment to maximize the likelihood of success. A convenient assay for predicting the success of chemotherapeutic protocols is available in the art (Weisenthal, L. M., et al., *Cancer Res* (1983) 43:749; Weisenthal, L. M., et al., *Cancer Treat Rep* (1986) 70:1283; Weisenthal, L. M., et al., *Adv Clin Oncol* (1989) in press). The assay described in these publications, known as the DiSC assay, specifically tests the effect of proposed chemotherapeutic protocols on the subject's own tumor cell populations by use of a contrast dye procedure. Other in vitro assays could also be utilized to direct therapy, (e.g., Kern and Weisenthal, *J Natl Cancer Inst* (1990) 82:582-88).

In general, the assay method requires preparation of microscope slides from mixtures of the tumor cells with a solution containing approximately 30,000 aldehyde-fixed duck red blood cells (DRBC). The DRBC are placed into the culture to be tested in 0.5 M NaCl containing Fast Green dye (for solid tumors) or Fast Green dye plus nigrosin dye (for hematologic neoplasms) such that the final dye concentrations after addition to the cell cultures are 0.5% and 0.25%, respectively. The cultures are transferred to a Cytospin centrifuge (Shandon, Sewickly, Pa.) and 10 minutes after addition of DRBC and dyes are agitated and deposited onto glass microscope slides in the Cytospin. The slides are then counterstained with either modified Haematoxylin-eosin (H & E) for solid tumors or Wright-Giemsa for hematologic neoplasms. In this process, living cells are stained with H & E or Wright-Giemsa, but dead cells are stained with Fast Green or Fast Green nigrosin. The effect of particular drugs can readily be determined by adding the proposed drug to the culture to be plated on the slides in this procedure.

Cell counts are done under the microscope by an experienced observer who can discern living lymphocytes and macrophages and DRBC. The total living cells are determined as the ratio of counts of living cells of each type divided by the counts of DRBC times 30,000, the number of DRBC added to the culture. Percent cell survival is calculated by dividing the number of living tumor cells present in the treated cultures by the number of living tumor cells present in the controls.

This DiSC assay is useful both for screening possible chemotherapeutic regimens for the intended subjects and for testing the effects of the immunopotentiators on the treated cells. In addition, as this is a microscopic technique, the presence of the required macrophage associated with the tumor cells in order to assure success by administration of the immunopotentiator can be ascertained.

Thus, one method to optimize choice of immunopotentiator and timing of administration utilizes cryopreservation of the primary tumor and performance of the DiSC assay using thawed cells and fresh peripheral blood monocytes obtained at various times during the tumor-destroying therapy.

As stated above, the immunopotentiator must be capable of stimulating macrophages. A partial list of presently contemplated immunopotentiators of this type is set forth in FIG. 1. The list is not intended to be exhaustive, and undoubtedly many additional immunopotentiators for macrophages will be discovered within the next few years. There is, however, a wide range of such compositions from which to choose, and any composition which causes the stimulation of macrophage activity is partially satisfactory. It is preferred to use immunopotentiators which are single compounds or defined mixtures thereof. However, complex extracts can also be used. Immunopotentiators with only limited capacity for macrophage activation, such as IL-2 and α-interferon are much less effective.

In the method of the invention, subjects are administered an effective amount of an immunopotentiator after having had successful results from tumor-destructive therapy such that a population of tumor-specific cytotoxic macrophages has been generated in the subject. This can be ascertained by performance of an in vitro assay, such as that described above, on cells withdrawn from the subject. The cell suspension used is examined to assure the presence of macrophages in association with it and then tested with the immunopotentiating agent. Subjects providing tumor specimens that contain macrophages capable of such response are then treated with the immunopotentiating agent. In the absence of accessible tumor tissue for biopsy (e.g., in the adjuvant chemotherapy situation) selection and timing of immunopotentiator administration must proceed without benefit of the assay, but it is important to: (1) administer an immunopotentiator capable of activating macrophages with tumor-specific cytotoxic potential and (2) administer said immunopotentiator chronologically following treatment with therapy for which there is a presumption of success.

The dosage level of the immunopotentiator depends, of course. on the immunopotentiator chosen and its toxicity, the condition of the patient, and the mode of administration. Typically, an approximate dosage level can be determined by in vitro determinations on the subject's own tumor cells and then extrapolated to amounts for administration to the subject depending on whether administration is local or systemic. Systemic administration is generally by injection, especially by intravenous injection or by oral administration. Localized administration may be topical or by local injection.

In addition, of course, the immunopotentiators of the invention may be formulated for administration using standard pharmacological methods, such as those set forth in *Remington's Pharmaceutical Sciences,* latest edition, Mack Publishing Company, Easton, Pa.

In addition to providing the immunopotentiators to those patients who have already exhibited successful results from tumor-destructive therapy, patient populations can be prepared for subsequent administration of the immunopotentiator by suitable therapeutic treatment included in the protocol. It is preferred to determine this protocol in accordance with the DiSC assay predictive measures described above. In this manner, an individual subject can be treated in a two step procedure resulting in tumor regression—the first step requiring the administration of a therapeutic regimen such as chemotherapy which is at least successful in generating tumor necrosis and formation of macrophages specific for the tumor, followed by administration of a macrophage immunopotentiator.

Figures 1, 3:
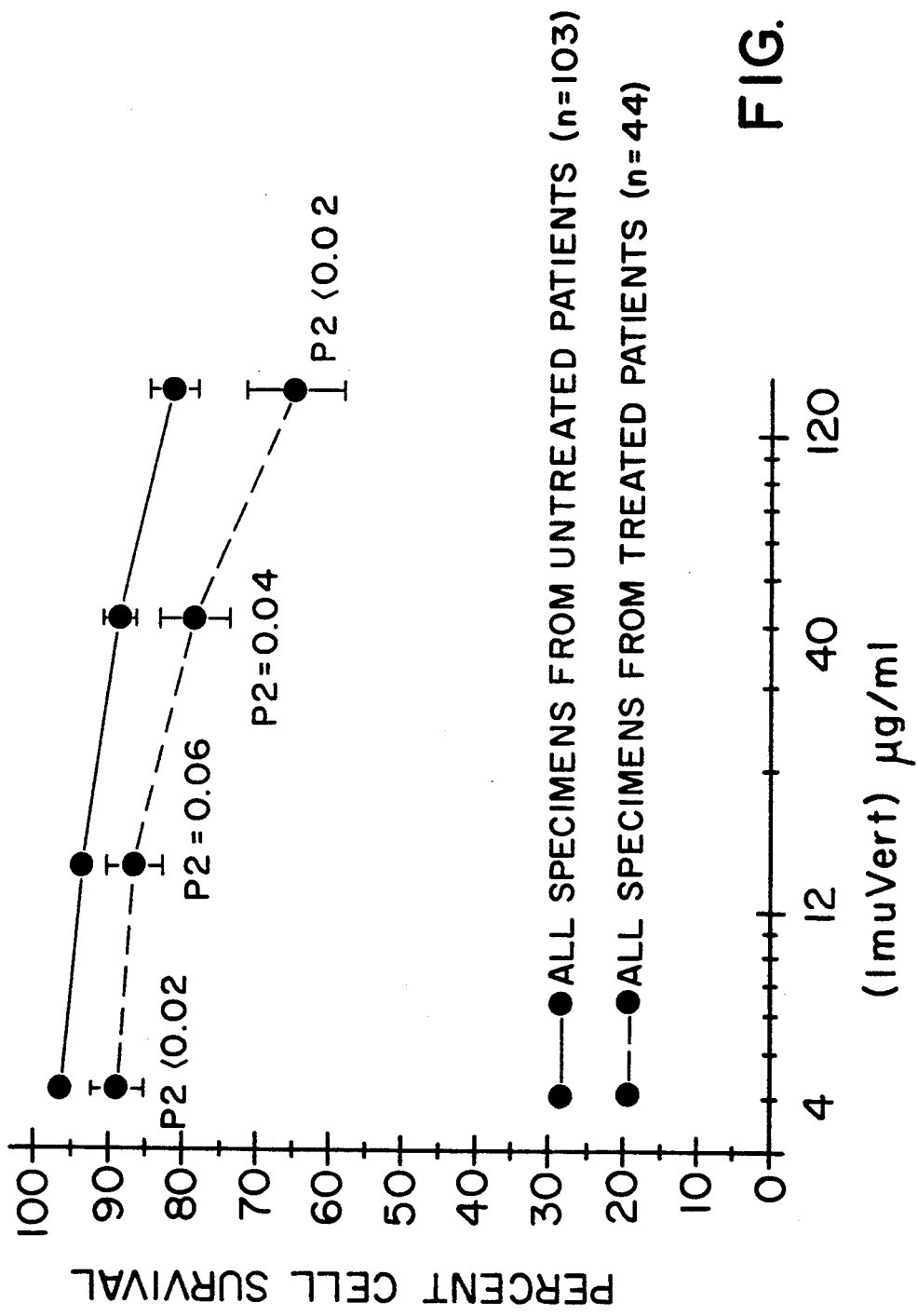
FIG. 3(1-3) shows a summary of the results of treatment with immunopotentiator depending on the treated or untreated nature of the patients receiving immunopotentiator, regardless of tumor nature.
Figures 2, 3:
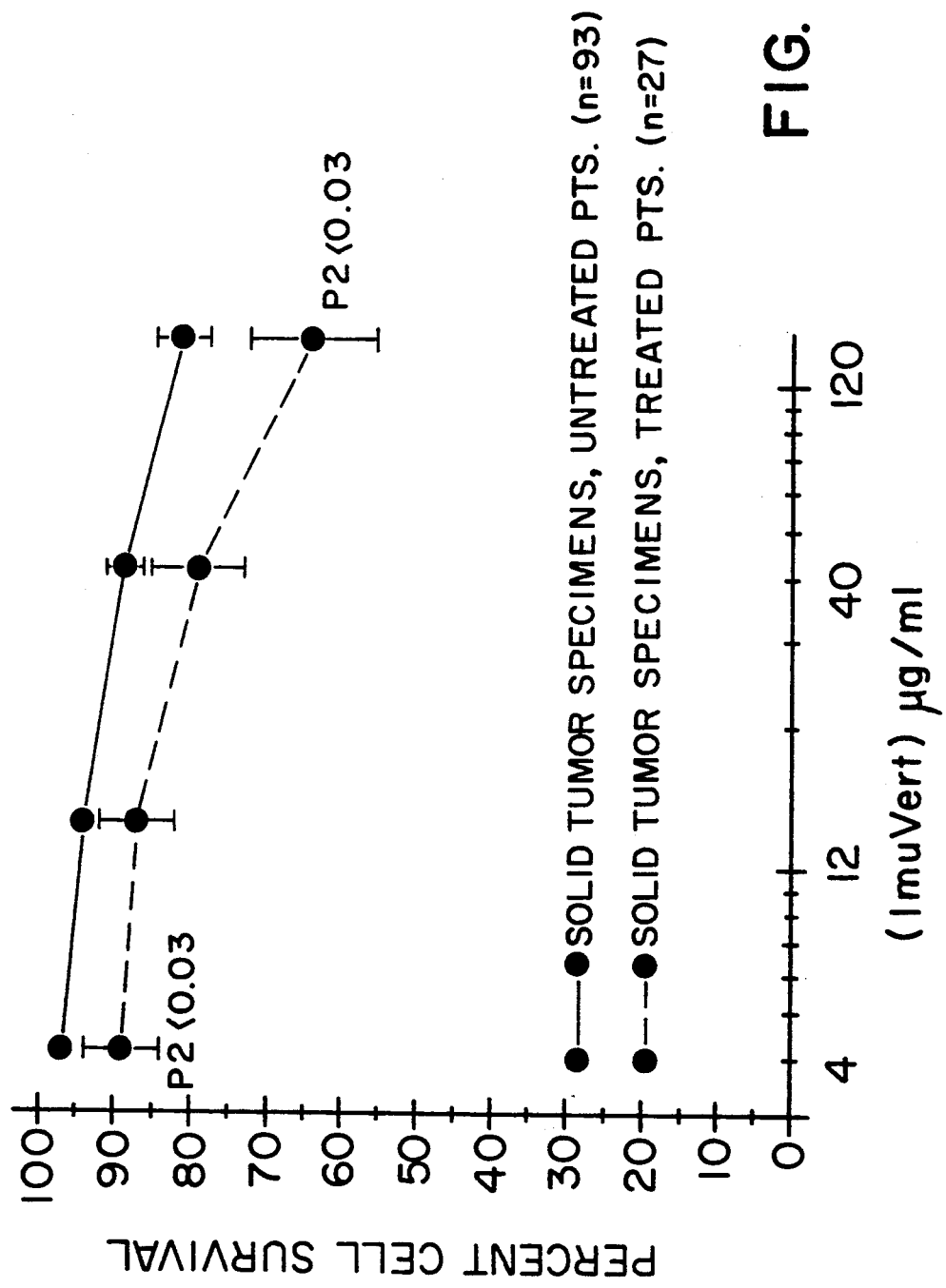
Figure 3:
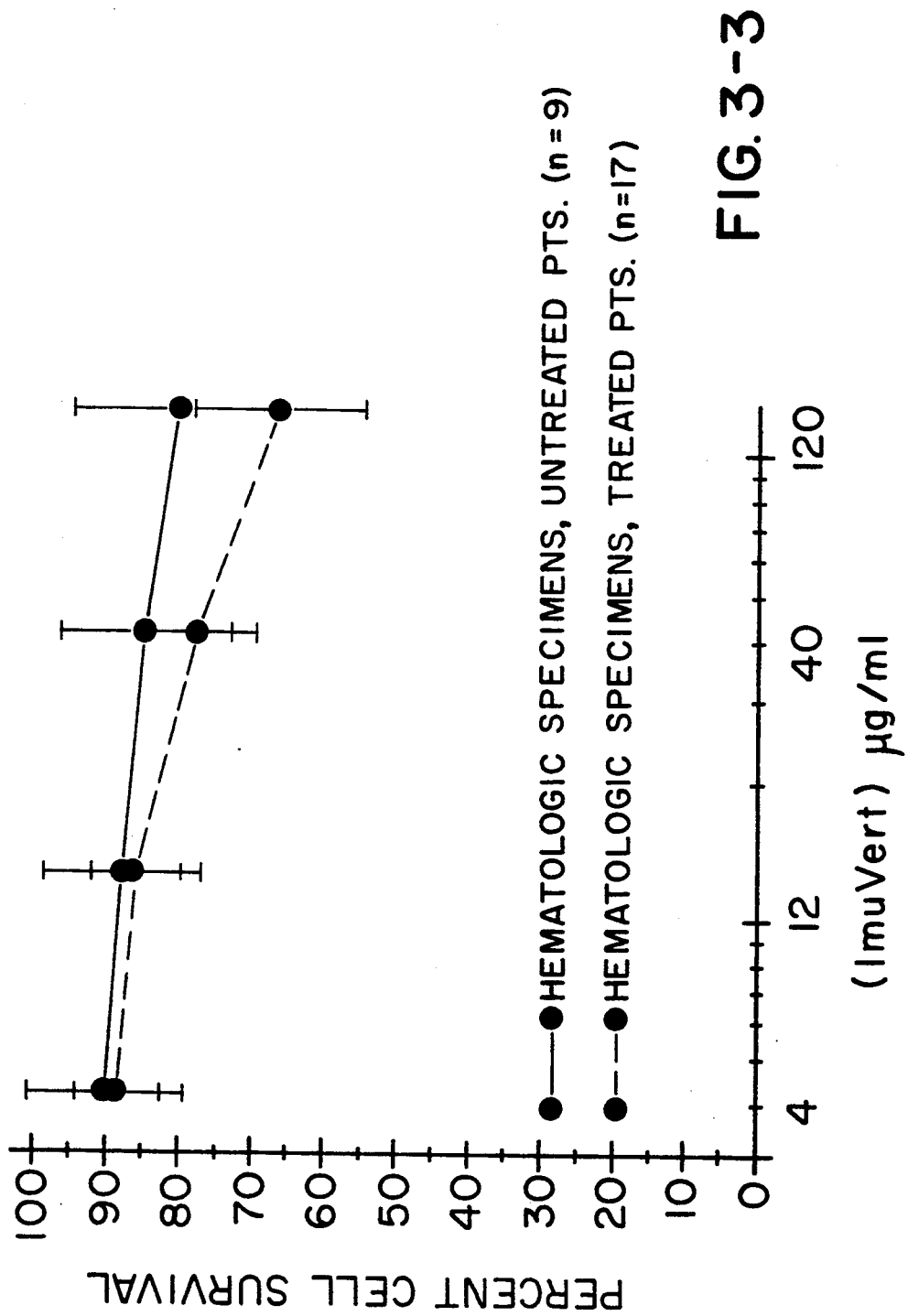

The examples below have shown, using the DiSC assay described above, that the success of treatment with an illustrative immunopotentiator known to stimulate macrophage correlates with the subject tumor cells having been successfully treated with chemotherapy. These results are summarized in FIG. 2. In this summary chart, it is clear that administration of the illustrative potentiator "ImuVert" is largely ineffective, even at high concentrations, against patients who are not treated by chemotherapy, whether their tumors are drug sensitive or resistant and further is largely ineffective with treated patients having drug-resistant tumors. Only the group having drug-sensitive tumors which have been successfully treated show a marked positive response to the potentiator. FIG. 3 shows similar overall results between treated and untreated patients, regardless of sensitivity. It is apparent that the difference between the successful and unsuccessful groups in this illustration is less than in FIG. 2 since the treated patients include those harboring tumors that are drug resistant.

The following examples are intended to illustrate but not limit the invention.

EXAMPLE 1

General Methods

Fresh tumor specimens, including solid tumor biopsies, malignant effusions, lymph node biopsies, bone marrow aspirates and peripheral blood specimens are obtained in the manner conventional for testing in vitro drug resistance by the Oncotech Central Laboratory, Irvine, Calif. The DiSC assay, described above, is referred to. All specimens except malignant effusions were in transport medium containing RPMI-1640, 15% fetal calf serum, pen/strep 100 U/ml/100 $\mu$g/ml and preservative-free heparin, 10 U/ml. (Blood specimens are aspirated initially to glass tubes containing EDTA.) Specimens are generally received within 24 hours of biopsy.

In further processing for the in vitro assay, solid tumors were dissociated by teasing and collagenase/deoxyribonuclease treatment; malignant effusions were collected by centrifugation, and blood and marrow specimens were centrifuged over Ficoll-diatrizoate to collect the viable mononuclear cells. After processing for in vitro drug resistance testing, cells left over from the in vitro assay were used in the procedures below.

The leftover cell suspensions were centrifuged over Ficoll-diatrizoate to minimize the number of nonviable cells plated and to reduce or eliminate contaminating blood cells and polymorphonuclear cells. The mostly viable, mononuclear cells, which include tumor cells, lymphocytes, macrophages and, where applicable, mononuclear bone marrow precursors, were collected at the interface and washed with complete RPMI-1640 medium and aliquoted into conical polypropylene microtubes for testing in a DiSC assay. In the procedures below, a modified form of the DiSC assay, conducted as described in Weisenthal, L. M., et al., *Cancer Treat Rep* (1986) 70:1283, referenced above, was used to test the effect of the immunopotentiators.

The assay begins by aliquoting the cells and either the control medium or medium containing the immunopotentiator into conical polypropylene microtubes. DiSC assay slides are prepared from a fraction of the samples, and the remaining culture tubes are placed into humidified 37° C. incubators at 5% $CO_2$. The cells are cultured with and without the immunopotentiator for a total of 6 days, and then another set of day 6 DiSC assay slides were prepared from all cultures. The general method for the preparation of assay slides has been described hereinabove and the procedure is further set forth in Weisenthal, et al., mentioned previously.

In more detail, tumor cell specimens are diluted with 6-10 volumes of complete RPMI-1640 medium containing 10 units/ml of heparin. This is underlayered with Ficoll-diatrizoate (Lymphocyte Separation Medium, Litton Bionetics, Kensington, Md.) and centrifuged. The interface layer is washed and counted. Solid tumors are manually teased apart after incubation with collagenase/DNAse. Cells (0.1-1 $\times 10^6$, depending on cell yield) are aliquoted into 4 ml capacity conical polypropylene tubes and brought to a volume of 0.9 ml with complete RPMI-1640 medium plus 10% heat-inactivated fetal calf serum; 0.1 ml of 10$\times$ drug solution is added to the cell suspensions, and cells are incubated with the immunopotentiator in the test samples for 6 days.

After 6 days in culture, 0.2 ml of a suspension of acetaldehyde-fixed duck red blood cells (DRBC), containing 30,000 DRBC, is added to each tube, and the cells are concentrated to a final volume of 0.2 ml by centrifugation. Following this, 0.2 ml of Fast Green (solid tumors) or Fast Green-Nigrosin (hematologic neoplasms) (1.0% Fast Green and 0.5% Nigrosin in 0.15 M NaCl) is added and the tubes are vortexed. After 10 min cell suspensions are again vortexed and cytocentrifuged (1200 rpm on a Cytospin I or 1080 rpm on a Cytospin II) for 8 min. The cell disks are then counterstained with Hematoxylin and eosin (H&E) (solid tumors) or are fixed with methanol for 20 sec and counterstained with Wright-Giemsa (hematologic neoplasms) in an automated slide stainer (Ames Hematek). Mounting balsam (Histomount, National Diagnostics, Somerville, N.J.) and coverslips are added. Slides are then counted at either 400× or 1000× on a standard light microscope by a trained hematology technologist. "Living" cells stained red with H&E or Wright-Giemsa. "Dead" cells stained green with Fast Green and black or black-green with Fast Green-Nigrosin. DRBC stain green and are easily identified as nucleated microelliptocytes. They are identified by their morphological characteristics—i.e., nucleation and elongate shape. Only "living" tumor cells and DRBC are counted. The "living" tumor cells/DRBC ratio is determined, and the ratios from immunopotentiator-treated cultures are compared with the ratios from control cultures (cultures containing only vehicle, usually 0.9% NaCl) and expressed as percent of control.

Differential cell counts were performed on the time 0 and day 6 slides as set forth above to obtain a percentage cell survival. In each case, the percentage is determined by the relationship of the slide containing the immunopotentiator with that used as a control. A total of 300 samples were tested.

EXAMPLE 2

Results of Individual Assays

As a general description, cells treated successfully by chemotherapy can be compared using the DiSC assay either not further treated or treated with 12 µM ImuVert. In the case of the cells not further treated, live cancer cells (which stain red) are readily seen. In the same cells, treated with ImuVert, only green-stained cells (dead cells) are readily apparent.

Figures 1, 4:
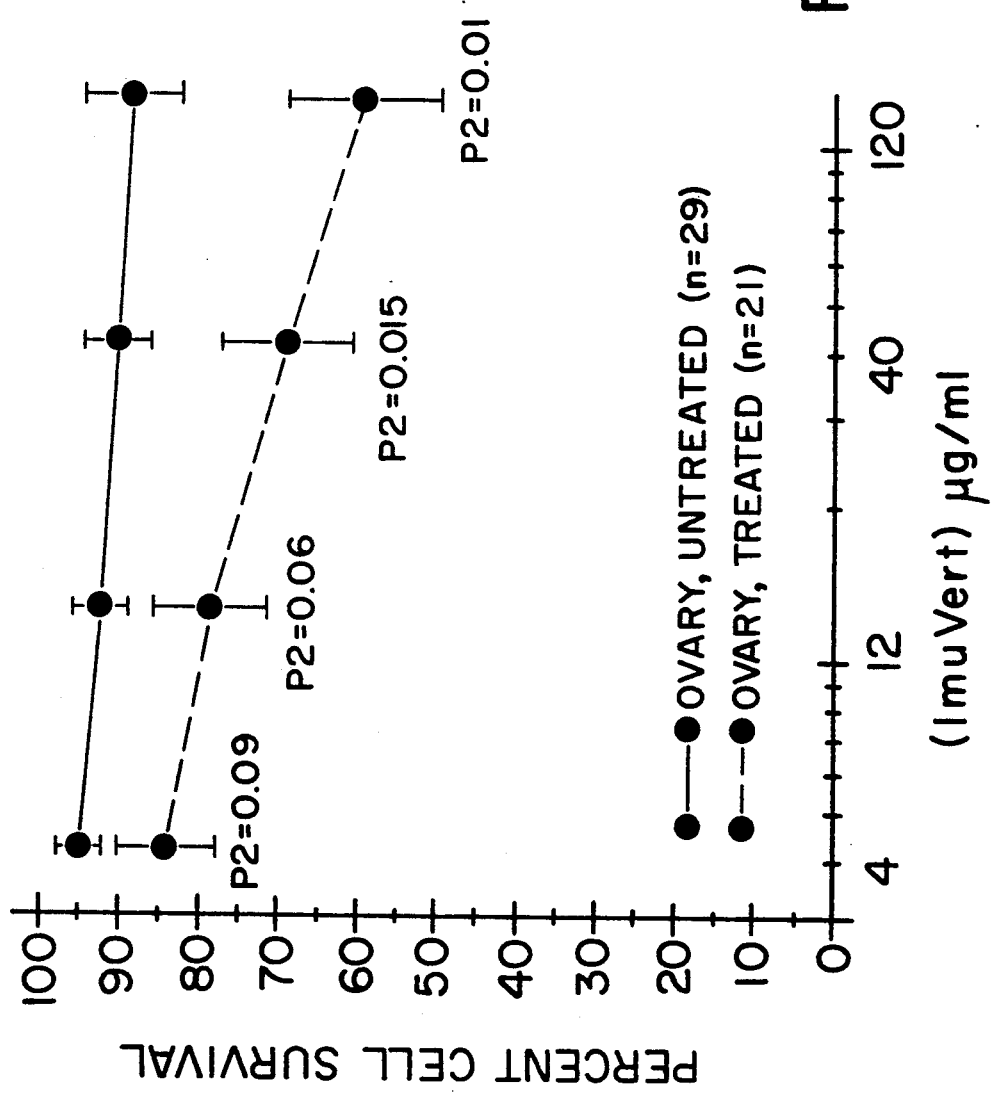
FIG. 4(1-2) shows the effect of prior chemotherapy on success of treatment of immunopotentiator for ovarian adenocarcinoma which is known to respond to chemotherapy.
Figures 2, 4:
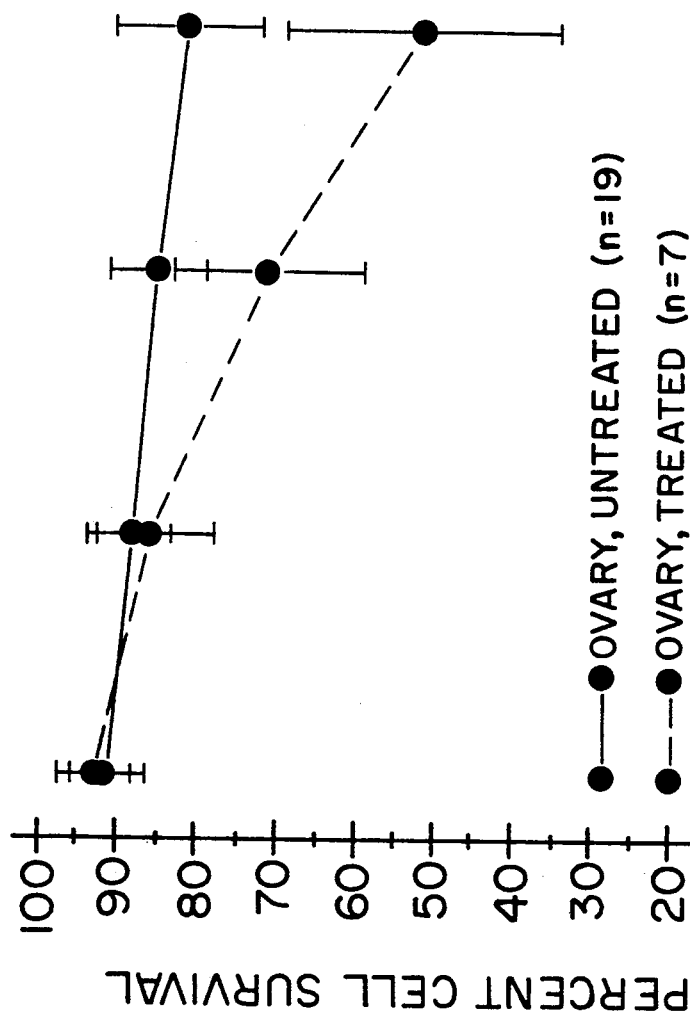

FIG. 4 shows a comparison of the activity of the potentiator ImuVert at various concentrations for breast adenocarcinomas as a function of whether the patient had or had not been treated.

Figures 1, 5:
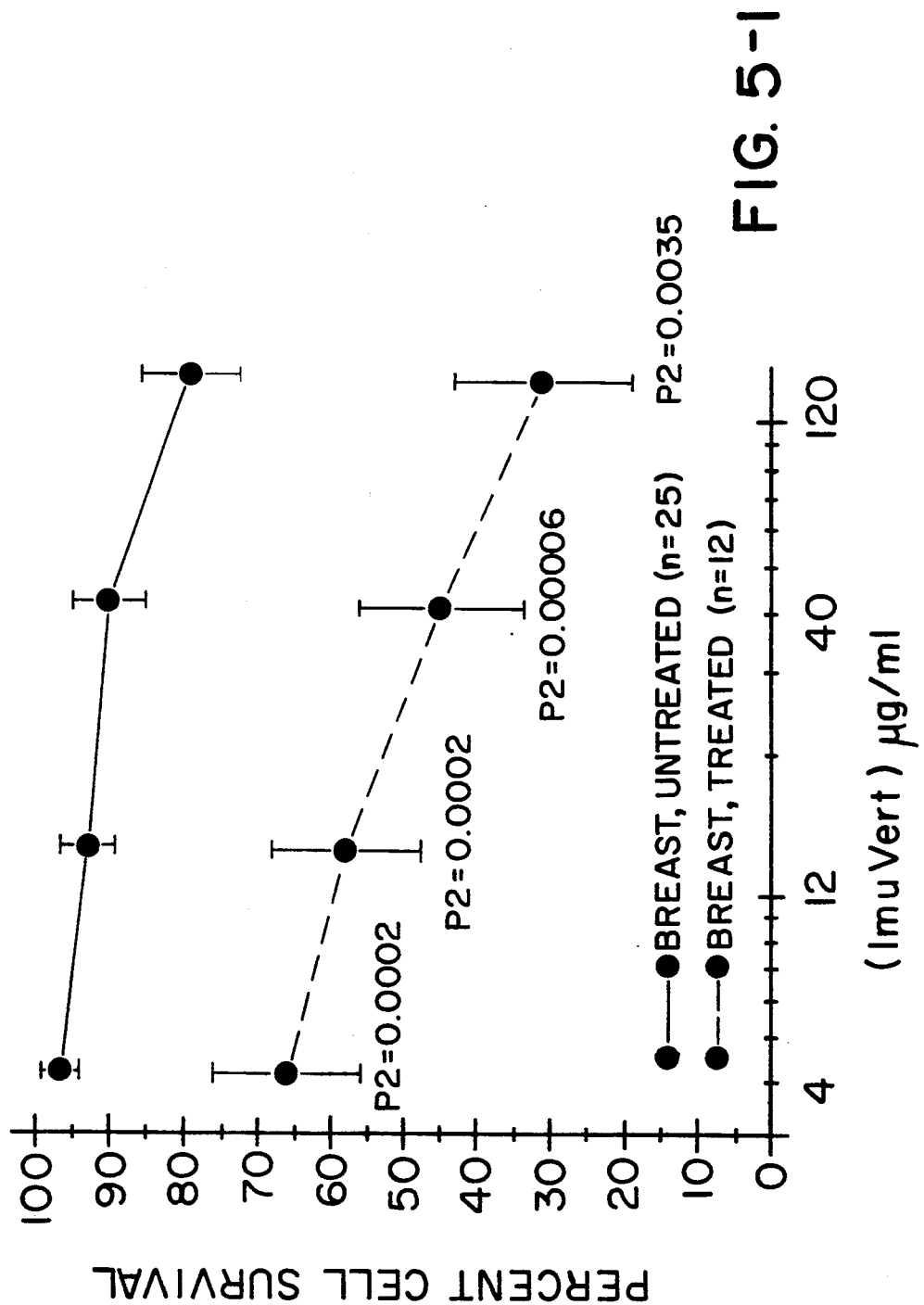
FIG. 5(1-2) is analogous to FIG. 5 but as applied to breast adenocarcinoma which is also sensitive to chemotherapy.
Figures 2, 5:
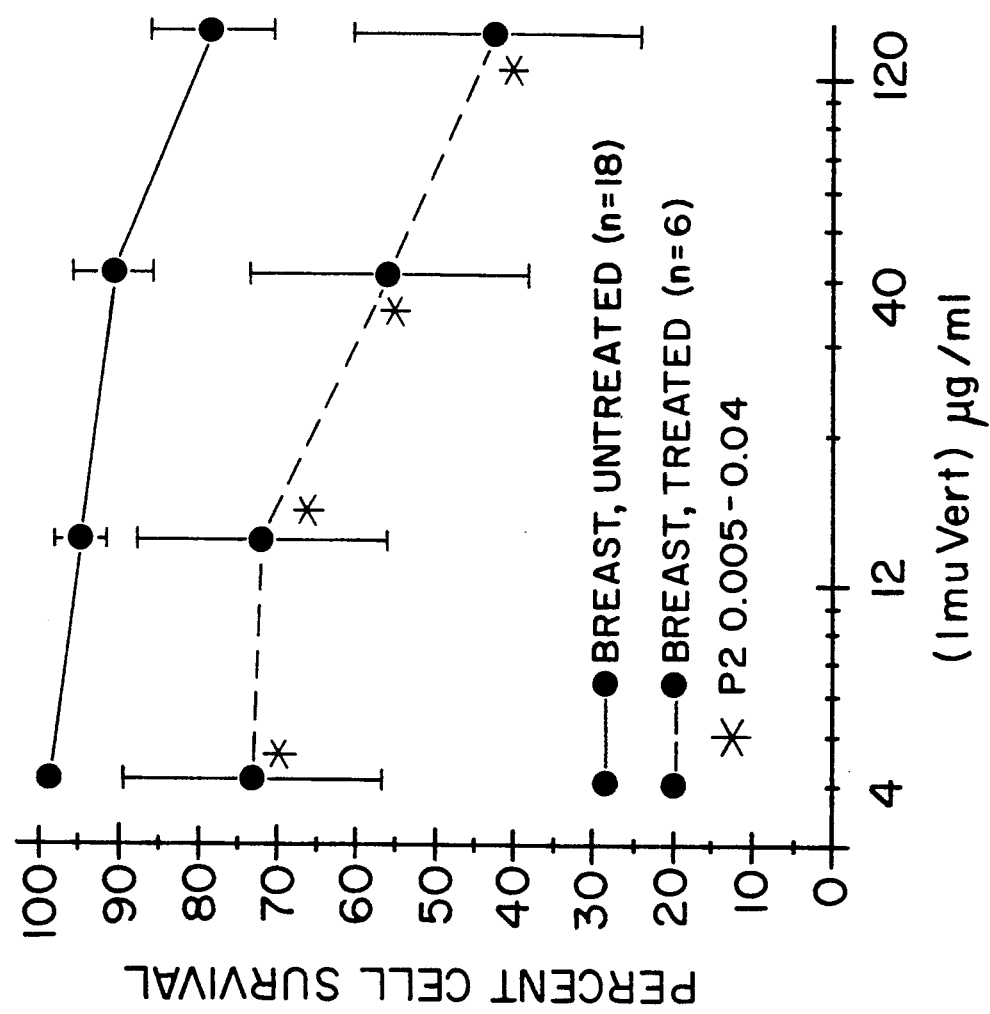
Figures 1, 6:
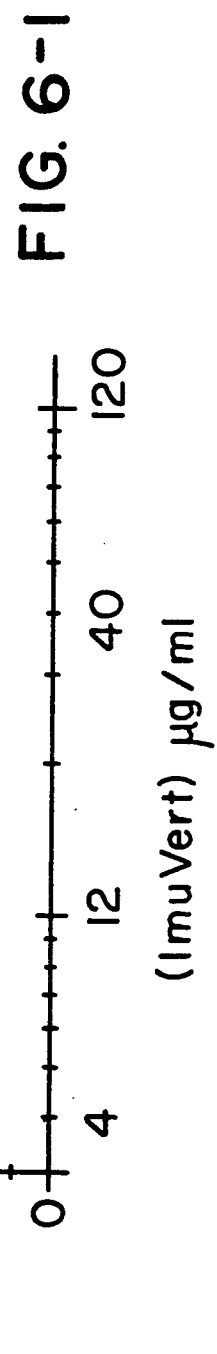
FIG. 6(1-2) is analogous to FIGS. 4 and 5, but as applied to colon adenocarcinoma which is known to be resistant to chemotherapy.
Figures 2, 6:
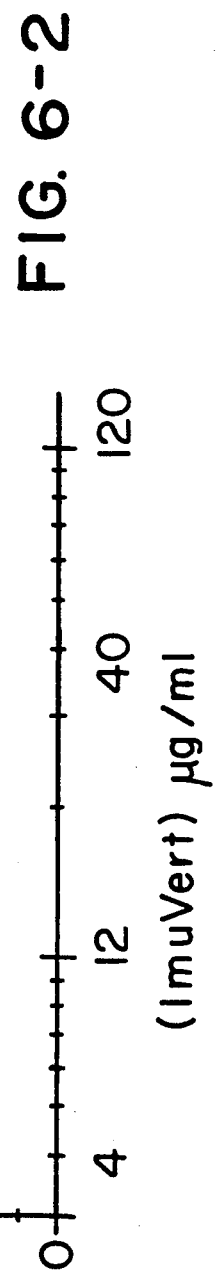
Figure 7:
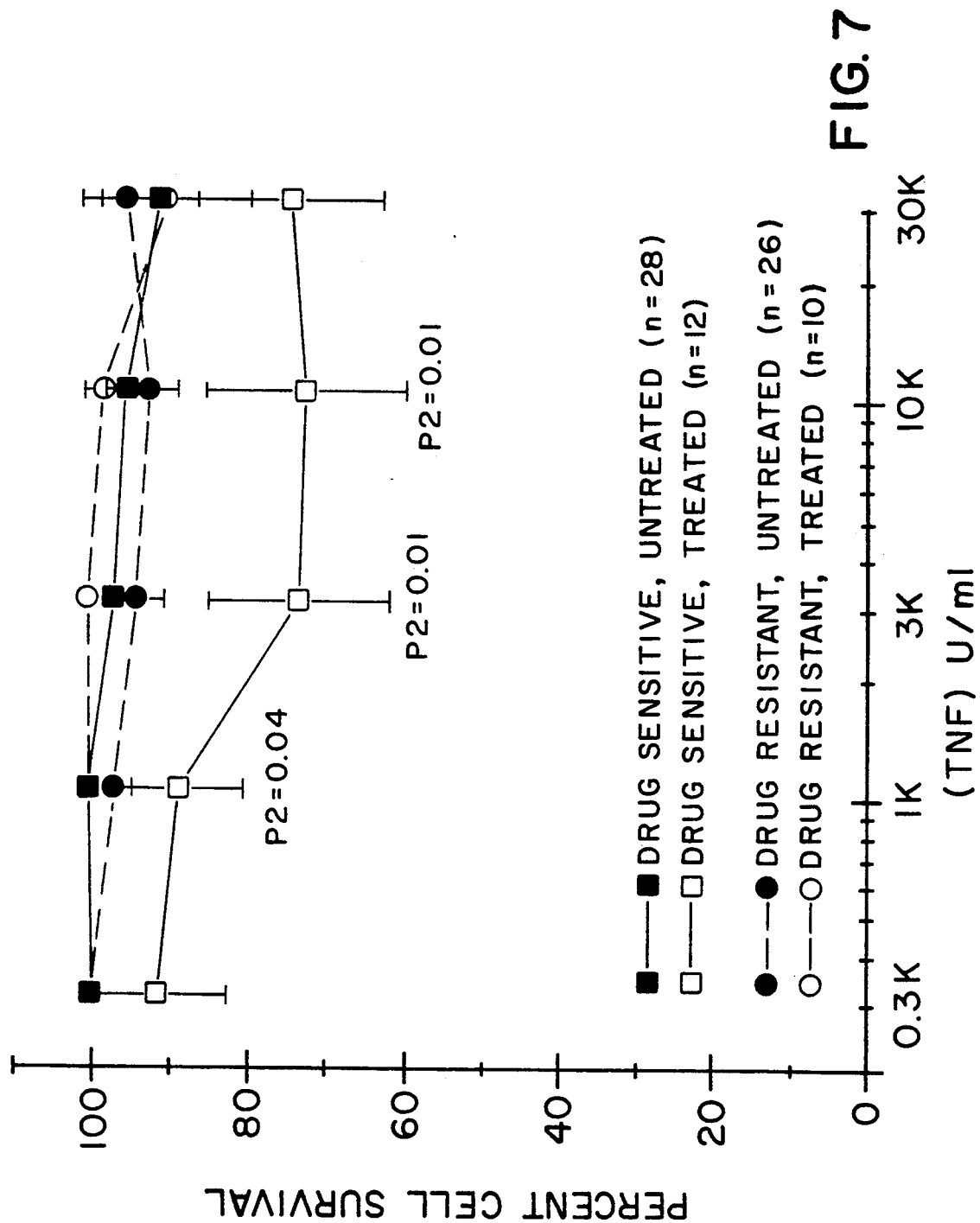
FIG. 7 shows a comparison similar to that shown in FIG. 2 using TNF as immunopotentiator.
Figure 8:
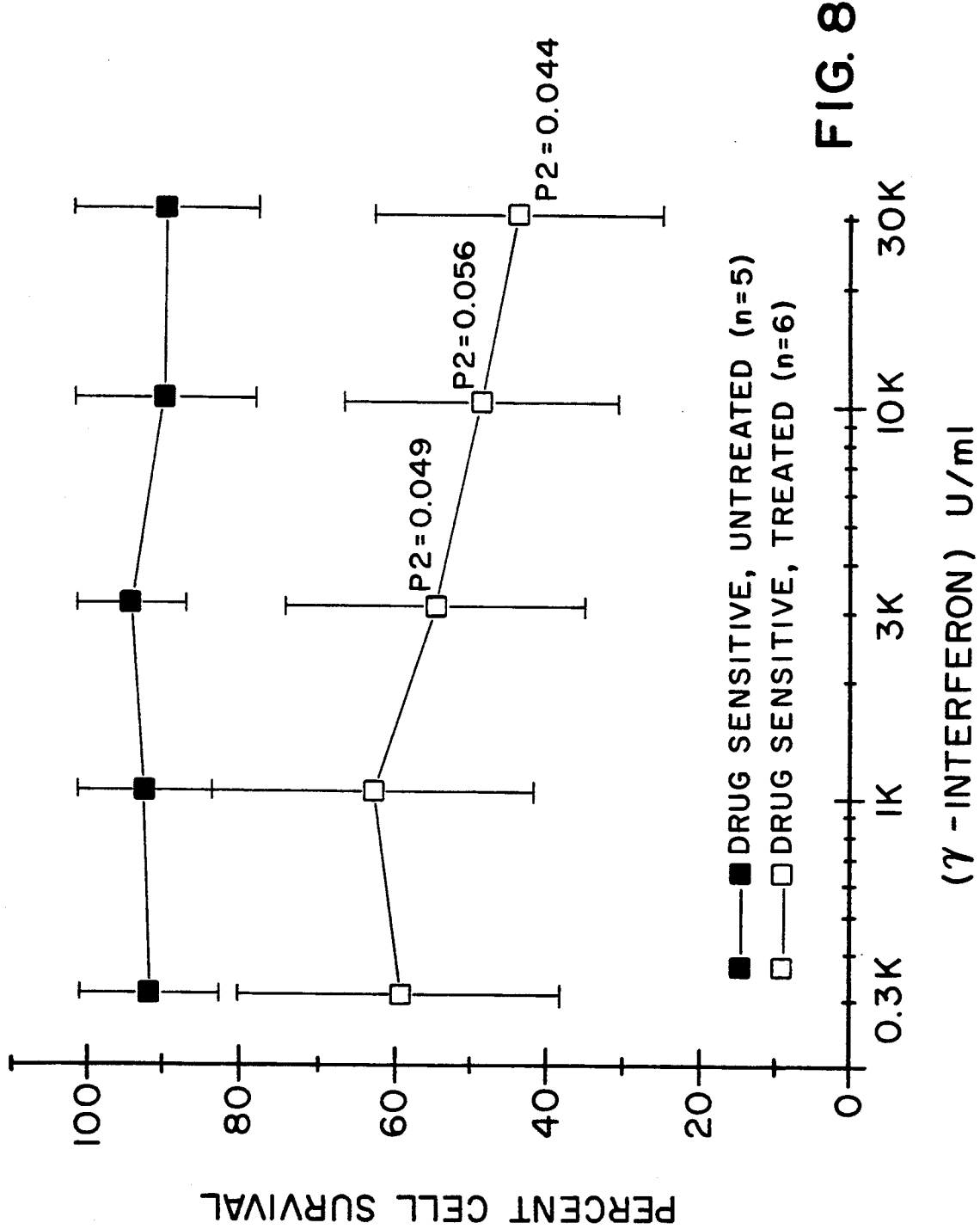
FIG. 8 shows a comparison similar to that shown in FIG. 1 using γ-interferon as immunopotentiator.
Figure 9:
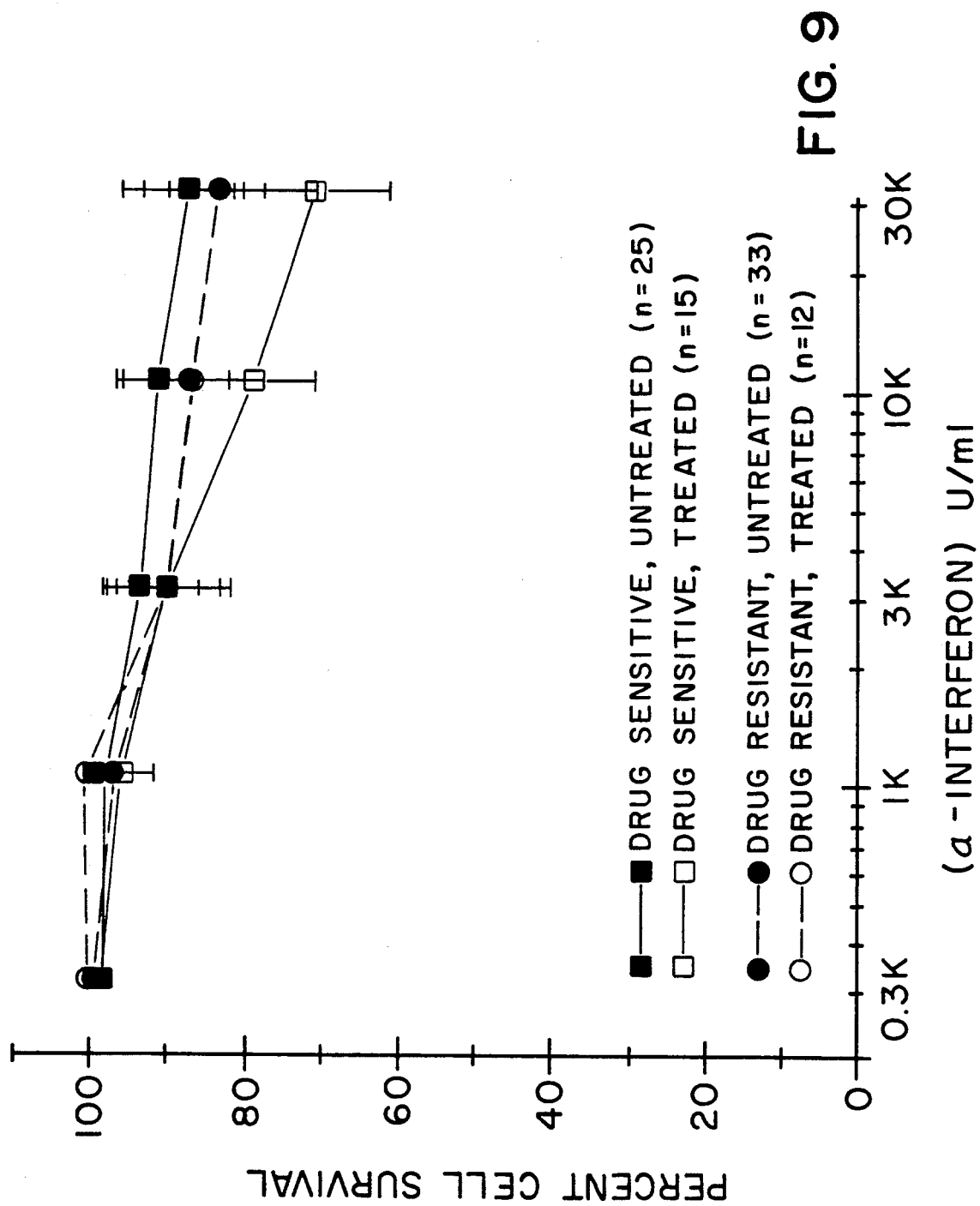
FIG. 9 shows a comparison similar to that shown in FIG. 1 using α-interferon as immunopotentiator.
Figure 10:
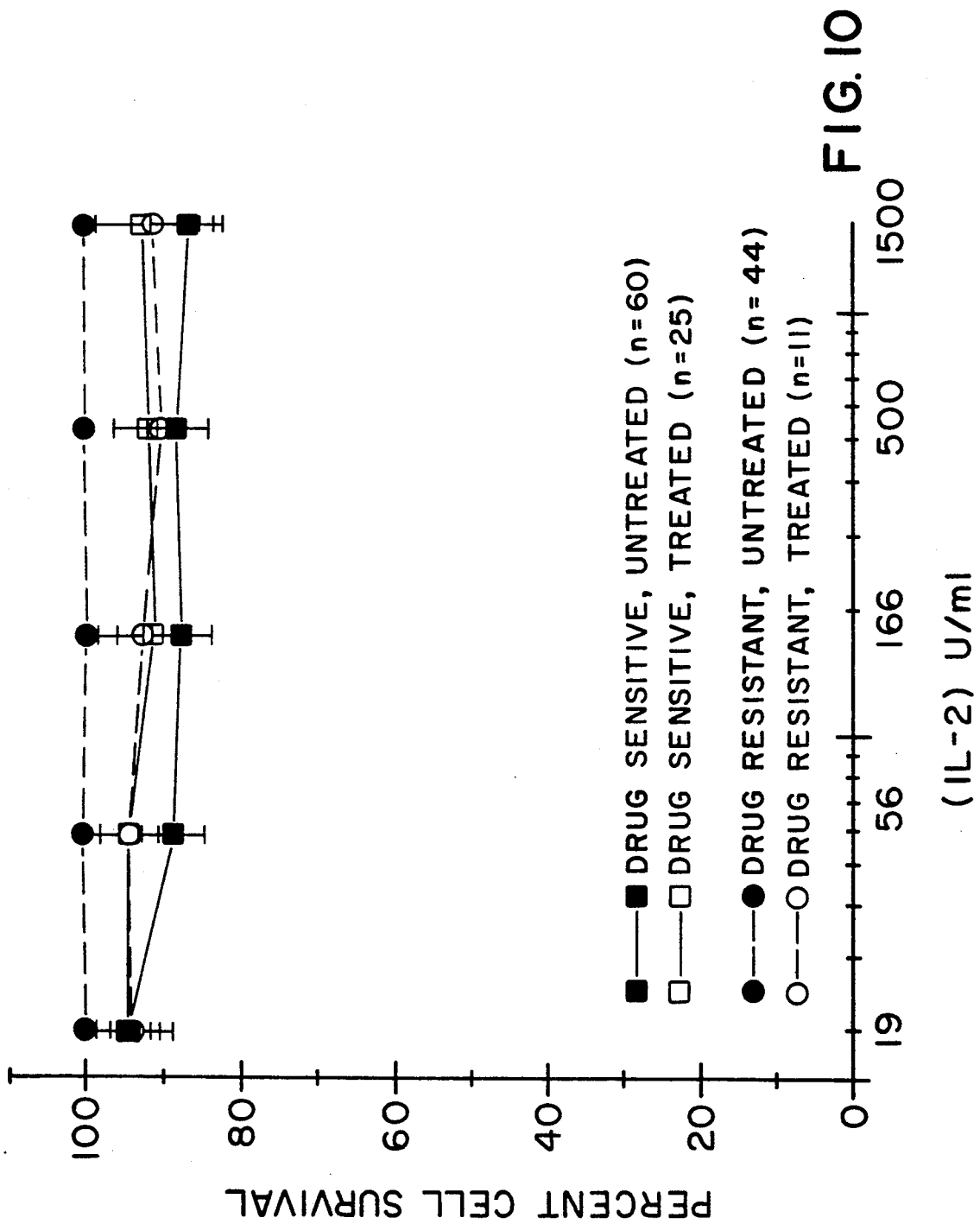
FIG. 10 shows a comparison similar to that shown in FIG. 1 using IL2 as immunopotentiator.

FIG. 5 shows similar results for ovarian cancer, and FIG. 6 for colon cancer. It is apparent that the treatment-sensitive breast and ovarian cancers which came from patients who had undergone chemotherapy show vastly improved responses from those obtained from untreated patients to treatment with ImuVert. In the resistant colon adenocarcinoma, little difference was observed between treated and untreated patients.

As described above, FIG. 2 showed the difference in response to ImuVert activity among four groupings of specimens—untreated specimens regardless of tumor sensitivity, treated drug-sensitive and treated drug-insensitive specimens.

Similar determinations were made with respect to additional immunopotentiators, TNF, γ-interferon, α-interferon, and IL2. As the results in FIGS. 7–10 show, the more potent the immunopotentiator is with respect to stimulating macrophage as opposed to lymphocytes, the greater the improvement in results for the treated sensitive tumors as compared to untreated tumors. Thus, treated sensitive tumors give marked responses to TNF and γ-interferon, but a relatively small response to α-interferon and no detectable response to IL2.

Further, the activity of ImuVert against fresh tumor specimens was abrogated by dexamethasone, thus showing that an immunosuppresant destroyed its effect. Dexamethasone should not interfere with a direct cytotoxic effect. In contrast to the immunopotentiators, directly cytotoxic chemotherapeutic agents (e.g., cisplatin and carboplatin) were significantly more active in specimens obtained from untreated ovarian cancer patients than in specimens from previously-treated patients. The above findings all support the conclusion that the results reported for the immunopotentiator are reflective of true differences in the tumor-immunity status of treated and untreated patients with chemotherapy-responsive neoplasms.

It has also been observed that the immunopotentiators are ineffective in tumor specimens which do not contain effector cells. There seems no relationship between the endogenous effector cell amount and activity of the immunopotentiators in the assay system, provided that at least *some* discernible macrophage effector cells were present. Samples with effector:tumor cell ratios of 0.02–1.0 behaved similarly. While it appeared that lymphocytes need not be present as effector cells, the results obtained indicated that macrophages must be present.

I claim:

1. A method to effect necrosis and/or regression in tumors which are responsive to tumor-destructive therapy, which method comprises:
    administering to a subject harboring said tumor cells therapeutic protocol effective to destroy at least a portion of said tumor cells and to induce production or activation of macrophages specific therefor, followed by
    administering to said subject, after a time period sufficient to permit the formation of said macrophages which are capable of specific toxicity to said tumor cells, an amount of an immunopotentiator for macrophage effective to cause said necrosis and/or regression.

2. The method of claim 1 which further includes testing tumor cells from said subject subsequent to therapy for the presence of macrophages capable of responding to said immunopotentiator with a tumor-specific cytolytic effect.

3. The method of claim 1 which further comprises assaying tumor cells from said subject prior to tumor-destructive therapy to determine effective therapeutic protocols for use in said therapy.

4. The method of claim 1 wherein said immunopotentiating agent is selected from the group consisting of the reagents set forth in FIG. 1.

5. The method of claim 1 wherein said immunopotentiating agent is nostatine.

6. The method of claim 1 wherein said tumor-destructive therapy is chemotherapy.

7. A method to effect a necrosis and/or regression in tumor cells, which method comprises administering to a subject harboring tumor cells responsive to tumor-destructive therapy, which subject has been effectively treated by said therapy so as to generate macrophages capable of specific cytotoxicity to said tumor cells an amount of an immunopotentiator which is capable of stimulating said macrophages to effect said regressive and/or necrotic response.

8. The method of claim 7 wherein said immunopotentiating agent is selected from the group consisting of the reagents set forth in FIG. 1.

9. The method of claim 7 wherein said immunopotentiating agent is nostatine.

* * * * *